(12) United States Patent
Koyama et al.

(10) Patent No.: US 8,231,642 B2
(45) Date of Patent: Jul. 31, 2012

(54) INTESTINAL ANASTOMOTIC SURGERY AID

(75) Inventors: Isamu Koyama, Saitama (JP); Shuro Hayashi, Tokyo (JP)

(73) Assignee: JMS Co., Ltd. (JP)

( * ) Notice: Subject to any disclaimer, the term of this patent is extended or adjusted under 35 U.S.C. 154(b) by 0 days.

(21) Appl. No.: 13/077,647

(22) Filed: Mar. 31, 2011

(65) Prior Publication Data
US 2011/0245853 A1    Oct. 6, 2011

Related U.S. Application Data

(63) Continuation of application No. 11/791,788, filed on May 29, 2007, now abandoned.

(30) Foreign Application Priority Data

Nov. 29, 2004    (JP) .................................. 2004-344727

(51) Int. Cl.
  *A61B 17/08* (2006.01)
  *A61B 17/10* (2006.01)
(52) U.S. Cl. ..................................... 606/153; 227/179.1
(58) Field of Classification Search ............... 227/175.1, 227/179.1, 180.1, 181.1, 179, 181, 190; 606/219, 606/153, 155
See application file for complete search history.

(56) References Cited

U.S. PATENT DOCUMENTS

| | | | |
|---|---|---|---|
| 4,574,806 A | 3/1986 | McCarthy | |
| 4,592,354 A | 6/1986 | Rothfuss | |
| 4,703,887 A | 11/1987 | Clanton et al. | |
| 5,139,513 A * | 8/1992 | Segato | 606/219 |
| 5,205,459 A | 4/1993 | Brinkerhoff et al. | |
| 5,309,927 A | 5/1994 | Welch | |
| 5,797,943 A | 8/1998 | Danks et al. | |

FOREIGN PATENT DOCUMENTS

| | | |
|---|---|---|
| JP | 60-099241 | 6/1985 |
| JP | 02-501275 | 10/1990 |
| JP | 06-209947 | 8/1994 |
| JP | 09-289990 | 11/1997 |
| JP | 11-004832 | 1/1999 |
| JP | 2000-166932 | 6/2000 |
| WO | 88/09644 | 12/1988 |
| WO | 2005/023092 A2 | 3/2005 |

OTHER PUBLICATIONS

International Search Report; PCT/JP2005/021856; Feb. 21, 2006.
Japanese Office Action; JP2004-344727; Nov. 16, 2010.

* cited by examiner

*Primary Examiner* — Corrine M McDermott
*Assistant Examiner* — Christina Lauer
(74) *Attorney, Agent, or Firm* — Studebaker & Brackett PC; Donald R. Studebaker

(57) ABSTRACT

An intestinal anastomotic surgery aid 1 is constituted with a cylindrical portion 40 for covering the proximal end side of an engaging rod 28, and a cover portion 41 that extends from the cylindrical portion 40 towards the distal end side of the engaging rod 28. The proximal end part of the cylindrical portion 40 is inserted to a recessed portion 26 of a device main body 21 to be held to the device main body 21. The anus-side piece of the intestine is tied with a suture to be held to the outer face of the cylindrical portion 40.

4 Claims, 13 Drawing Sheets

INTESTINAL ANASTOMOTIC SURGERY AID

CROSS-REFERENCE TO RELATED APPLICATIONS

This application is a continuation of U.S. Patent Application Ser. No. 11/791788 filed on May 29, 2007 and entitled "Intestinal Anastomotic Surgical Aid" which is now abandoned.

TECHNICAL FIELD

The present invention relates to an intestinal anastomotic surgery aid that is used in an intestinal anastomotic surgery for anastomosing an intestine that is cut into two by, for example, a surgical operation with the use of an anastomotic device.

BACKGROUND ART

Conventionally, surgical operations have been performed for removing, for example, a diseased part when a cancer is contracted on the large intestine of a human being. The intestine is cut into two in such surgical operation, so that an intestinal anastomotic surgery is necessary to anastomose the anus-side piece of the intestine connected to the anus and the stomach-side piece of the intestine connected to the stomach. When performing the intestinal anastomotic surgery, an anastomotic device that is disclosed in Patent Document 1, for example, is used.

The anastomotic device disclosed in Patent Document 1 uses a large number of metallic staplers to anastomose the anus-side piece and the stomach-side piece of the intestine, and the device comprises a cylindrical device main body and an umbrella-shaped head that is detachably attached to the device main body. The device main body is inserted to the anus-side piece of the intestine from the anus. A large number of slits from which the staplers are struck out are formed in the outer circumference of the end face in the inserting direction of the device main body, and a ring-shaped cutter is provided on the inner side of each slit. Further, a recessed portion for housing intestine cutout pieces is formed on the inner side than the cutter in the end face of the device main body. Furthermore, at the center part of the end face of the above-described device main body, an engaging rod that projects towards the inserting direction of the device main body is provided in a state to be capable of being retracted into the device main body. Moreover, the above-described head comprises a projected portion to be engaged with the engaging rod of the device main body.

When performing the intestinal anastomotic surgery by using the anastomotic device described above, the device main body is inserted first from the engaging rod into the anus-side piece of the intestine. When the device main body is inserted to a prescribed position, the open end of the anus-side piece of the intestine is tied to the engaging rod with a suture as if to cover the device main body while maintained in the prescribed position. In the meantime, the open end of the intestine is closed by, for example, suturing after inserting the head into the stomach-side piece of, the intestine, while driving the projected portion of the head towards the outside by piercing through the side wall of the stomach-side piece of the intestine.

Then, when the engaging rod is retracted inside the device main body after engaging the projected portion of the head with the engaging rod of the device main body, the open end of the anus-side piece of the intestine and the side wall of the stomach-side piece of the intestine come into close contact with each other. The staplers struck out from the device main body at this time are pressed and bent by the head, after piercing through the open end of the anus-side piece of the intestine and the side wall of the stomach-side piece of the intestine. With this, the anus-side piece and the stomach-side piece of the intestine, are anastomosed and, at the same time, part of the intestine on the inner side than the anastomosed part is removed by the cutter of the device main body and placed in the recessed portion used for housing intestine pieces. Upon this, the anus-side piece and the stomach-side piece of the intestine are connected. Thus, use of the anastomotic device eliminates the need for the surgeon to perform a suturing treatment by using a needle and a suture when anastomosing the intestines. Therefore, it is possible to shorten the time of surgery and to perform the anastomotic surgery easily even in a part within the pelvis cavity where it is difficult to reach by hands.

Patent Document 1: Japanese Unexamined Patent Publication 11-4832 (p 2, p 3, FIG. 5)

DISCLOSURE OF THE INVENTION

Problems that the Invention is to Solve

In Patent Document 1, however, the anus-side piece of the intestine is directly held at the engaging rod of the device main body, so that the anus-side piece of the intestine is to slide on the outer face of the engaging rod from the point where the engaging rod is started to be retracted to the point where the retraction is ended. When the anus-side piece of the intestine slides on the outer face of the engaging rod like this, the anastomosed part of the anus-side piece of the intestine may be deformed and shifted from the device main body. If that happens, the anastomosed part of the anus-side piece of the intestine and that of the stomach-side piece of the intestine are not closely fitted with each other, so that the both may not be anastomosed in a desired manner.

Further, when the anus-side piece of the intestine is directly held at the engaging rod of the device main body as described above, the open end of the anus-side piece of the intestine needs to be pulled until reaching the outer face of the engaging rod. Therefore, when the length of the anus-side piece of the intestine becomes short because the diseased part is cut out from the part of the intestine closer to the anus, for example, it becomes difficult to pull the open end of the anus-side piece of the intestine until reaching the outer face of the engaging rod to be held thereby. As a result, it may become impossible to perform an anastomotic surgery by using the anastomotic device.

The present invention has been designed in view of the aforementioned issues. An object of the present invention therefore is to anastomose the anus-side piece and the stomach-side piece of the intestine in a desired manner by restricting the shift in the position of the anastomosed part of the anus-side piece of the intestine, which may be caused when retracting the engaging rod through which the device main body and the head are engaged. In addition, it is an object of the present invention to provide an intestinal anastomotic surgery aid, which makes it possible to use the anastomotic device even when the length of the anus-side piece of the intestine is short.

Means of Solving the Problems

In order to achieve the foregoing objects, in the present invention, a cylindrical portion that covers the engaging rod on the device main body side is held by the device main body, and the anus-side piece of the intestine is held on the outer face of the cylindrical portion.

Specifically, a first aspect of the present invention is drawn to an intestinal anastomotic surgery aid used for an anastomotic surgery for anastomosing two cutout pieces of an intestine including an anus-side piece and a stomach-side piece, the anastomotic surgery being performed using an anastomotic device including a device main body inserted from an anus to the anus-side piece of the cutout intestine and a head inserted to the stomach-side piece of the cutout intestine, either one of the device main body and the head having an engaging rod projecting therefrom, the protruding engaging rod then being engaged with the other one of the device main body and the head and retracted into the device main body thereby anastomosing the anus-side piece and the stomach-side piece of the intestine, the intestinal anastomotic surgery aid being attached to the device main body of the anastomotic device.

The intestinal anastomotic surgery aid is structured such that the intestinal anastomotic surgery aid comprises a cylindrical member that covers the device main body side of the engaging rod while maintaining a distance from an outer face, of the engaging rod, while the device main body and the engaging rod are being integrated, wherein the cylindrical member is held to the device main body, and the anus-side piece of the intestine is held to an outer face of the cylindrical member.

With this structure, the anus-side piece of the intestine is held to the outer face of the cylindrical member that is held to the device main body, while the device main body is being inserted to a prescribed position of the anus-side piece of the intestine via the anus. In this state, since the cylindrical member is formed to cover the engaging rod while maintaining a distance from the outer face of the engaging rod and is formed in a larger diameter than the engaging rod, it requires to pull only a shorter length of the anus-side piece of the intestine compared to the conventional case where the anus-side piece of the intestine is held directly to the engaging rod. This makes it possible to have the intestine held at the device main body through the cylindrical member, even if the length of the anus-side piece of the intestine cannot be secured long enough because the diseased part in the vicinity of the anus is cut out, for example.

Further, since the anus-side piece of the intestine is held to the cylindrical member that covers the engaging rod as described above, the anus-side piece of the intestine does not slide on the outer face of the engaging because of the retracting action of the engaging rod. With this, the anastomosed part of the anus-side piece of the intestine is not to be deformed, and it becomes possible to locate the anastomosed part at a prescribed position of the device main body. As a result, the anastomosed part of the anus-side piece of the intestine and that of the stomach-side piece of the intestine can securely be fitted with each other closely, when the engaging rod is retracted completely into the device main body.

A second aspect of the present invention is the intestinal anastomotic surgery aid of the first aspect of the present invention, which is structured in such a manner that: the engaging rod is provided to project from the device main body towards an inserting direction of the device main body; and a cover member for covering a distal end part of the engaging rod is detachably provided to the cylindrical member.

With this structure, the distal end part of the engaging rod of the device main body is covered by the cover member. Thus, the distal end part of the engaging rod does not abut against the side wall and the like of the intestine to stick therein, when inserting the device main body to the anus-side piece of the intestine. By detaching the cover member from the cylindrical member after inserting the device main body into the prescribed position of the anus-side piece of the intestine, the distal end part of the engaging rod is exposed. With this, the head can be engaged with the engaging rod.

A third aspect of the present invention is drawn to an intestinal anastomotic surgery aid used for an anastomotic surgery for anastomosing two cutout pieces of an intestine including an anus-side piece and a stomach-side piece, the anastomotic surgery being performed using an anastomotic device including a device main body inserted from an anus to the anus-side piece of the cutout intestine and a head inserted to the stomach-side piece of the cutout intestine, the device main body having an engaging rod projecting therefrom, the protruding engaging rod then being engaged with the head and retracted into the device main body thereby anastomosing the anus-side piece and the stomach-side piece of the intestine, the intestinal anastomotic surgery aid being attached to the device main body of the anastomotic device.

The intestinal anastomotic surgery aid is structured such that: the intestinal anastomotic surgery aid comprises a cylindrical portion that covers the device main body side of the engaging rod while maintaining a distance from an outer face of the engaging rod, while the device main body and the engaging rod are being integrated; and a cover portion for covering a distal end part of the engaging rod by extending from the cylindrical portion towards the distal end side of the engaging rod, wherein: the cylindrical member is held to the device main body, and the anus-side piece of the intestine is held to an outer face of the cylindrical member; and the cover portion is detachably integrated with the cylindrical portion.

As in the case of the first embodiment, with this structure, the anus-side piece of the intestine is held to the outer face of the cylindrical portion that is held to the device main body in this structure, while the device main body is being inserted to the anus-side piece of the intestine. Thus, it is possible to have the intestine held at the device main body through the cylindrical portion, even if the length of the anus-side piece of the intestine cannot be secured long enough. Further, the anus-side piece of the intestine does not slide on the outer face of the engaging rod because of the retracting action of the engaging rod. Therefore, the anastomosed part of the anus-side piece of the intestine and that of the stomach-side piece of the intestine can securely be fitted with each other closely, when the engaging rod is retracted completely into the device main body.

Further, the distal end part of the engaging rod of the device main body is covered by the cover portion when the intestine anastomotic surgery aid is attached to the device main body. Thus, the distal end of the engaging rod does not abut against the side wall and the like of the intestine to stick therein, when inserting the device main body to the anus-side piece of the intestine. By detaching the cover portion from the cylindrical portion after inserting the device main body into the prescribed position of the anus-side piece of the intestine, the distal end part of the engaging rod is exposed. With this, the head can be engaged with the engaging rod.

A fourth aspect of the present invention is the intestinal anastomotic surgery aid of, the third aspect of the present invention, which is structured in such a manner that the cover portion is provided with a protector portion for preventing the distal end part of the engaging rod from piercing therethrough.

With this structure, it is possible to prevent the distal end part of the engaging rod from piercing through the cover portion, when inserting the device main body to the anus-side piece of the intestine.

A fifth aspect of the present invention is the intestinal anastomotic surgery aid of the fourth aspect of the present invention, which is structured in such a manner that an outer face of the protector portion is covered by a material that is softer than a material used for forming the protector portion.

For securely preventing the distal end part of the engaging rod from piercing through the cover portion by forming the protector portion with a hard material, it is possible with this structure to perform low-invasive anastomotic surgery, since the material that is softer than the protector portion is abutted against the side wall of the intestine when inserting the device main body to the anus-side piece of the intestine.

A sixth aspect of the present invention is the intestinal anastomotic surgery aid according to any one of the third to fifth aspects of the present invention, which is structured in such a manner that: the anus-side piece of the intestine is tied with an elastic member to be held to the outer face of the cylindrical portion; and the cylindrical portion is provided with an reinforcing portion for suppressing crushing deformation of the cylindrical portion in a radial direction.

With this structure, crushing deformation of the cylindrical can be suppressed. Therefore, the anus-side piece of the intestine can belied securely to the cylindrical portion with the elastic member.

A seventh aspect of the present invention is the intestinal anastomotic surgery aid according to any one the third to sixth aspects of the present invention, which is structured in such a manner that: the cylindrical portion is inserted and held to a recessed portion provided on an end face in an inserting direction of the device main body; and the cylindrical portion is provided with a fragile portion that is crush-deformed by being pressed by the head and the device main body which come close to each other, when the engaging rod is retracted into the device main body to anastomose the anus-side piece and the stomach-side piece of the intestine.

With the present invention, the fragile portion of the cylindrical portion is crushed towards the center line direction when anastomosing the anus-side piece and the stomach-side piece of the intestine, so that the size of the cylindrical portion in the center line direction becomes shorter.

An eighth aspect of the present invention is the intestinal anastomotic, surgery aid according to any one of the third to sixth aspects of the present invention, which is structured in such a manner that the outer face of the cylindrical portion is provided with an engaging portion with which the anus-side piece of the intestine tied with the elastic member is engaged.

With the present invention, the anus-side piece of the intestine tied to the cylindrical portion with the elastic member is engaged with the engaging portion. Thus, the anus-side piece of the intestine does not come off from the cylindrical portion. Further, when having the anus-side piece of the intestine held to the cylindrical portion at a position within the pelvis cavity where it is difficult to be visually checked and difficult to be reached by hands, it becomes possible to securely hold the intestine at a prescribed position of the cylindrical portion by engaging the intestine with the engaging portion.

Effect of the Invention

With the first aspect of the present invention, the anus-side piece of the intestine is held to the outer face of the cylindrical member that is formed to cover the engaging rod. Thus, it is possible to perform the anastomotic surgery by using the anastomotic device, even in the case where the length of the anus-side piece of the intestine cannot be secured long enough because the diseased part in the vicinity of the anus is cut out, for example. Further, since the anus-side piece of the intestine is held to the cylindrical member formed in a shape to cover the engaging rod, the position of the anus-side piece of the intestine is not shifted when the engaging rod is retracted to the inside the device main body. Therefore, the anus-side piece and the stomach-side piece of the intestine can be anastomosed in the desired manner.

With the second aspect of the present invention, the distal end part of the engaging rod can be covered by the cover member. Thus, the device main body can be inserted to the anus-side piece of the intestine smoothly.

Like the first aspect of the present invention, it is possible with the third aspect of the present invention to perform the anastomotic surgery by using the anastomotic device, even in the case where the length of the anus-side piece of the intestine is short. At the same time, the anus-side piece and the stomach-side piece of the intestine can be anastomosed in the desired manner. Further, the distal end part of the engaging rod can be covered by the cover member, so that the device main body can be inserted to the anus-side piece of the intestine smoothly.

With the fourth aspect of the present invention, it is possible to prevent the distal end part of the engaging rod from piercing through the cover portion, when inserting the device main body to the anus-side piece of the intestine. This makes it possible in advance to avoid the engaging rod from abutting against the side wall of the intestine, thereby allowing the intestinal anastomotic surgery to be performed safely.

With the fifth aspect of the present invention, the protector portion is covered with a material that is softer than the material used for forming the protector portion. Therefore, it is possible to perform low-invasive intestinal anastomotic surgery, while securely preventing the engaging rod from piercing through the cover portion.

With the sixth aspect of the present invention, it is possible to suppress crushing deformation of the cylindrical portion with the reinforcing portion. Thus, the anus-side piece of the intestine can securely be tied to the cylindrical portion with the elastic member. Therefore, the anus-side piece of the intestine does not come off from the cylindrical portion, and the anus-side piece and the stomach-side piece of the intestine can be anastomosed securely.

With the seventh aspect of the present invention, the fragile portion of the cylindrical portion is crushed and the size thereof in the center line direction becomes shorter when anastomosing the anus-side piece and the stomach-side piece of the intestine. Therefore, the cylindrical portion does not intervene in the anastomosis performed between the anus-side piece and the stomach-side piece of the intestine, thereby allowing the both intestines to be anastomosed smoothly.

With the eighth aspect of the present invention, the anus-side piece of the intestine tied to the cylindrical portion is engaged with the engaging portion. Thus, it is possible to securely prevent the anus-side piece of the intestine from being shifted from a prescribed position of the cylindrical portion. Furthermore, the anus-side piece of the intestine can be held to the prescribed position of the cylindrical portion within the pelvis cavity where it is difficult to perform a hand work.

BRIEF DESCRIPTION OF THE DRAWINGS

FIG. 4 illustrates an enlarged reinforcing portion, in which

FIG. 13 illustrates an intestinal anastomotic surgery aid according to a second embodiment of the present invention, in which

Figure 1:
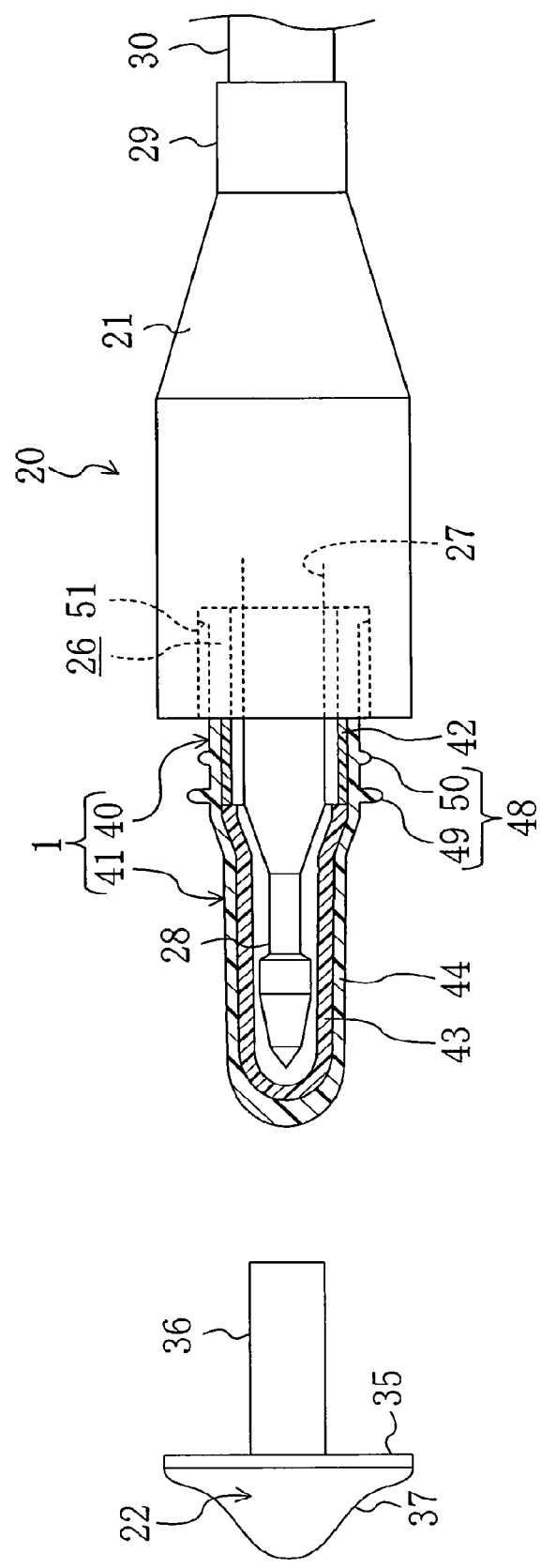
FIG. 1 is a fragmentary sectional view showing an intestinal anastomotic surgery aid and an anastomotic device according to a first embodiment of the present invention.

DESCRIPTION OF NUMERALS 1 intestinal anastomotic surgery aid
20 anastomotic device
21 device main body
22 head
26 recessed portion
28 engaging rod
40 cylindrical portion
41 cover portion
42 reinforcing portion
43 protector portion
48 engaging portion
70 cylindrical portion
71 cover portion
A anus-side intestinal
B stomach-side piece
C surgical suture (elastic member)
E anus

BEST MODE FOR CARRYING OUR THE INVENTION

In the followings, embodiments of the present invention will be described in details by referring to the accompanying drawings.

First Embodiment

FIG. 1 shows an intestinal anastomotic surgery aid 1 according, to a first embodiment of the present invention. For explaining this embodiment, an anastomotic device 20 will be described first before describing the intestinal anastomotic surgery aid 1.

Figure 2A:
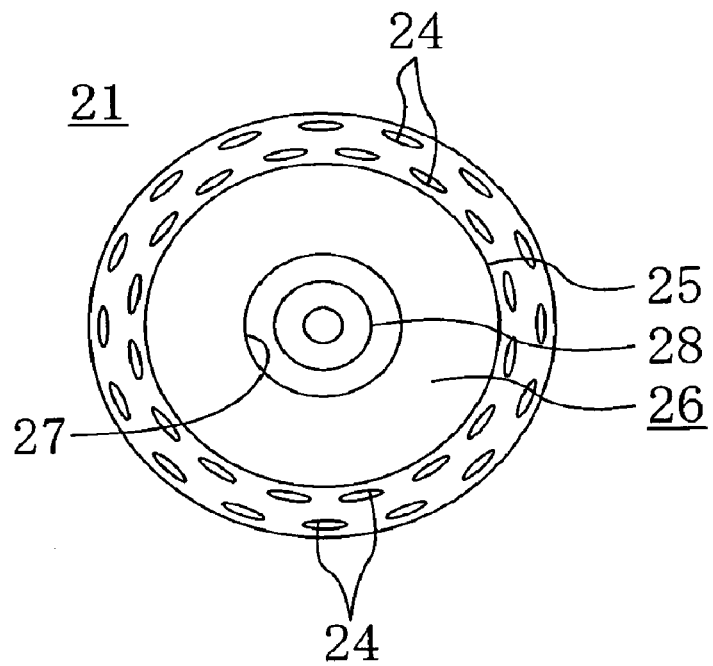
FIG. 2A is a front elevational view of a device main body of the anastomotic device when viewed from the distal end side of an engaging rod.

The anastomotic device 20 comprises a device main body 21 that is inserted to an anus-side intestinal A among the cut intestines (shown in FIG. 5A), and a head 22 that is inserted to a stomach-side piece B of the intestine. The device main body 21 is formed in substantially a cylindrical shape. As shown in FIG. 2A, a large number of slits 24 from which metallic staplers 23 (shown in FIG. 10) are struck out are formed in the outer circumference of the end face in the inserting direction of the device main body 21, and a ring-shaped cutter 25 is provided on the inner side than the slits 24 in the end face of the device main body 21. The blade edge of the cutter 25 is positioned on substantially the same plane as the end face of the device main body 21.

Further, a recessed portion 26 for housing the intestine pieces is formed on the inner side than the cutter 25 in the end face of the device main body 21. The bottom face of the recessed portion 26 extends substantially orthogonally to the center line of the device main body 21, and a hole portion 27 is, provided at the center of the bottom face, to which an engaging rod 28 is inserted. This engaging rod 28 is formed with a metallic material such as stainless steel, for example, and it is formed to extend straight towards the center line direction of the device main body 21. As shown in FIG. 1, the middle part of the engaging rod 28 in the longitudinal direction is formed thinner than the proximal end part and the distal end part thereof. Further, the proximal end part is formed to have a smaller diameter than the distal end part. Furthermore, the distal end part of the engaging rod 28 is formed acutely.

Further, an actuator (not shown) for driving the above-described engaging rod 28 back and forth in the center line direction is provided inside the device main body 21. This actuator is that of a known structure, which operates by a supply of electricity. A connector 29 is provided on the opposite side with respect to the inserting direction of the device main body 21, to which an end of a code 30 for supplying the electricity to the above-described actuator is connected. Furthermore, the anastomotic device 20 comprises a controller (not shown) for supplying the electricity to the actuator, and the other end of the above-described code 30 is connected to the controller. When the electricity is supplied from the controller and the actuator retracts the engaging rod 28, the engaging rod 28 is drawn into the device main body 21 to be housed therein. In the meantime, as shown in FIG. 1, when the actuator drives out the engaging rod 28, the engaging rod 28 is projected from the recessed portion 26.

Further, a large number of staplers 23 are enclosed inside the device main body 21 by corresponding to the layout of the slits 24. Each stapler 23 is formed substantially in a U-shape, and arranged in such a manner that the open side thereof faces towards the outer side from the slit 24. Furthermore, a striking mechanism (not shown) for striking out the staplers by the operation of the above-described actuator is enclosed inside the device main body 21.

Further, the head 22 is formed substantially in an umbrella shape, which comprise a circular plate member 35 formed to correspond, to the end-face shape in the inserting direction of the device main body 21, a projected portion 36 that projects towards the center line direction from the center part of the circular plate member 35 to be engaged with the above-described engaging rod 28, and a swollen member 37 formed to swell out on the opposite Side with respect to the projected portion 36 of the above-described circular plate member 35.

Figure 2B:
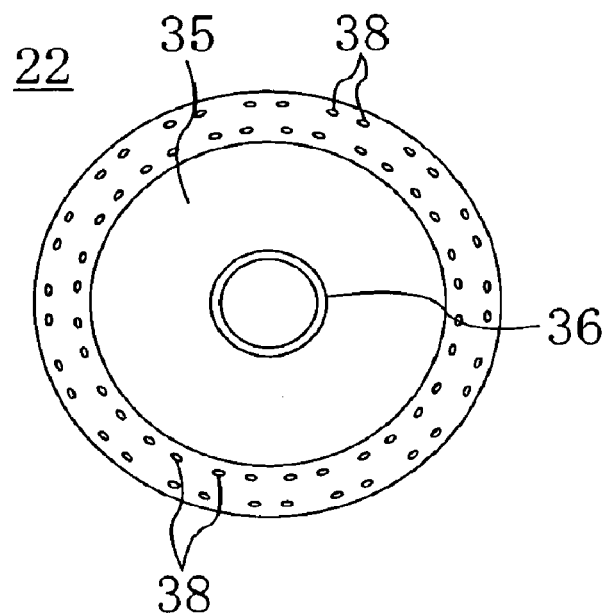
FIG. 2B is a front elevational view of a head when viewed from the distal end side of a projected portion.

The above-described circular plate member 35 is formed by molding a metallic material such as stainless steel, for example, and a large number of pits 38 are formed by corresponding to the above-described slits 24 in the outer circumference of the surface that faces towards the device main body 21, as shown in FIG. 2B. These pits 38 are for pressing and bending the open-side ends of the staplers 23 that are struck out from the slits 24. Further, the blade edge of the cutter 25 of the above-described device main body 21 is to abut against the inner side than the pits 38 of the circular plate member 35.

Further, the above-described projected portion 36 is formed by molding the same metallic material as that of the circular plate member 35, and the above-described engaging rod 28 is inserted to the inner side of the projected portion 36. The projected portion 36 is provided with an engaging mechanism (not shown) for preventing it from being detached from the engaging rod 28 by being engaged to, the middle part in the longitudinal direction of the inserted engaging rod 28. Furthermore, the above-described swollen member 37 is formed by molding a resin material, and it is fixed to the above-described circular plate member 35.

Figure 3:
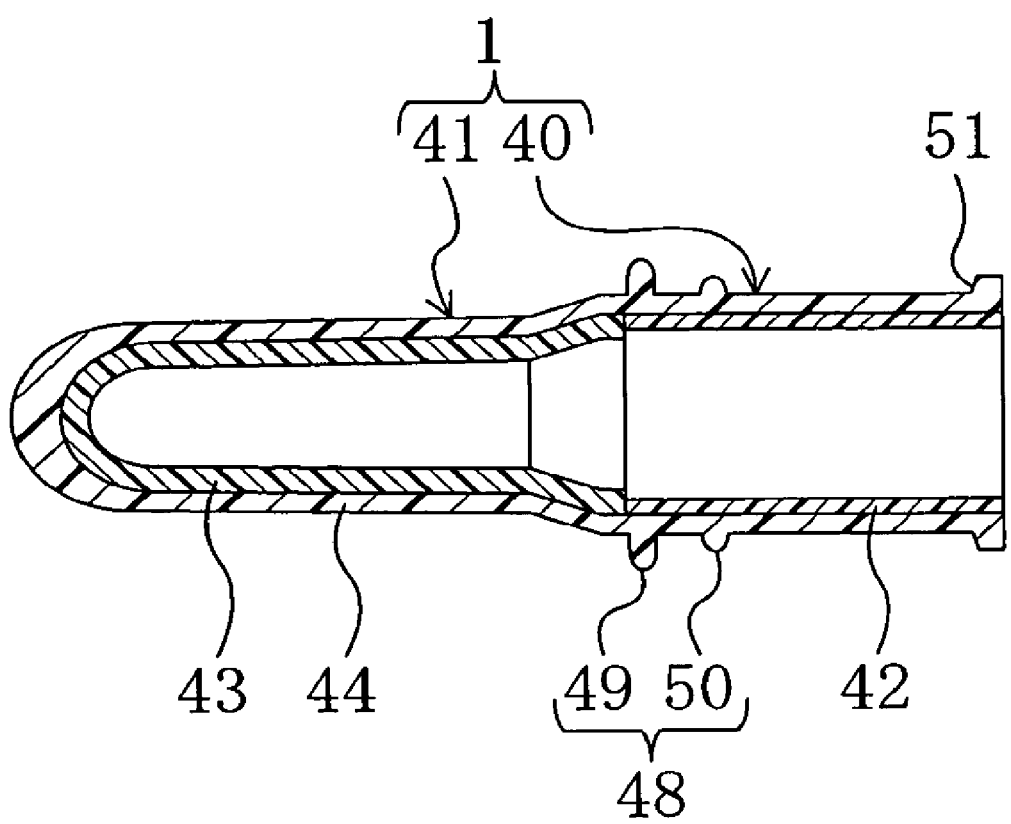
FIG. 3 is a sectional view of the intestinal anastomotic surgery aid.
Figure 6:
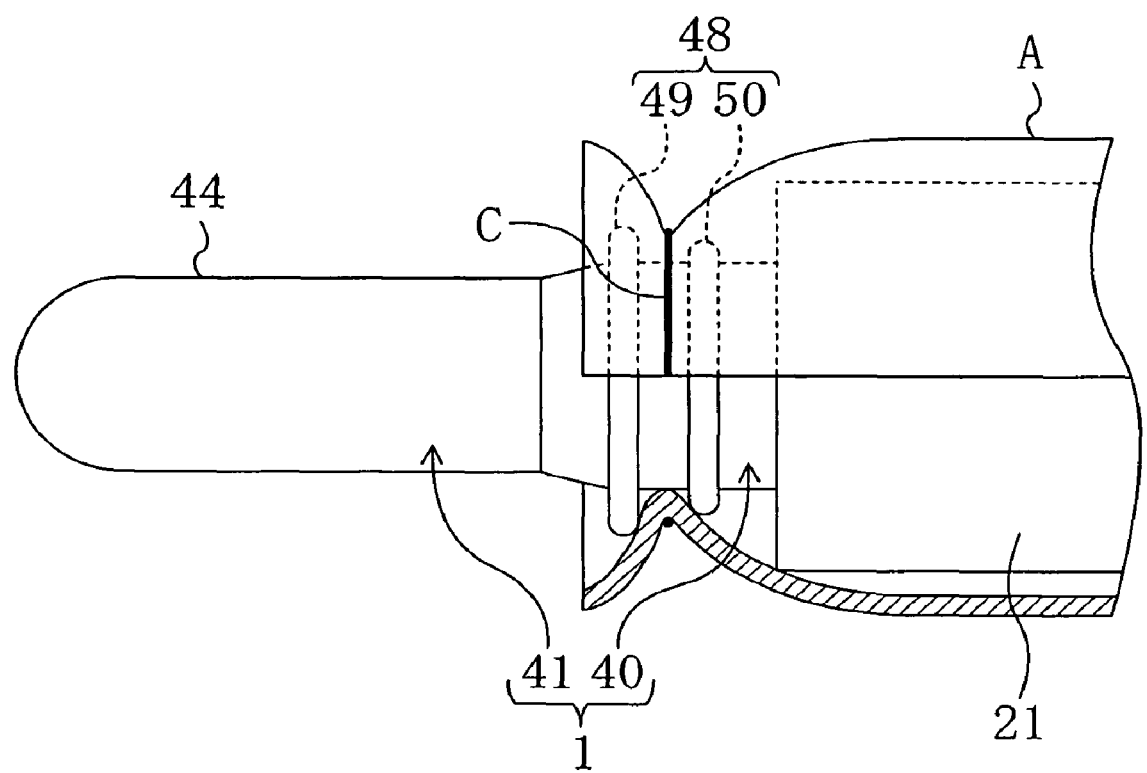
FIG. 6 is a fragmentary sectional view showing an enlarged view of the state where the anus-side piece of the intestine is tied to a cylindrical portion.

Next, the structure of the intestinal anastomotic surgery aid 1 will be described. As shown in FIG. 1 and FIG. 3, the structure of the intestinal anastomotic surgery aid 1 is formed in a cylindrical shape as a whole, and the entire length is set to be within a range of about 40 mm to 50 mm by corresponding to the shape of the above-described anastomotic device 20. The above-described intestinal anastomotic surgery aid 1 comprises a cylindrical portion 40 for covering the proximal end side of the above-described engaging rod 28, and a cover portion 41 for covering the distal end side of the engaging rode 28 by being extended towards the distal end, side of the engaging rod 28 continuously from the cylindrical portion 40. The cylindrical portion 40 has a circular cross section, and the outer diameter is set as about 11 mm. The cylindrical portion 40 is formed in such a manner that the inner face is distant from the outer face of the above-described engaging rod 28, and the anus-side piece A of the intestine is held at the outer face of the cylindrical portion 40 by being tied with a surgical suture C that is an elastic member, as shown in FIG. 6. Further, the cover portion 41 is formed in a cylindrical shape with a bottom, and the outer diameter is set as about 9 mm.

Each of the above-described cylindrical portion 40 and the cover portion 41 is formed in a double-layered structure. The inner layer of the cylindrical portion 40 is constituted with a reinforcing portion 42 for restricting crushing deformation of the cylindrical portion 40 in the radial direction. Meanwhile, the inner layer of the cover portion 41 is constituted with a protector portion 43 for preventing the engaging rod 28 from piercing through the cover portion 41. Furthermore, the outer faces of the above-described reinforcing portion 42 and the protector portion 43 are covered by an outer layer portion 44 that is fitted closely with the outer faces thereof to integrate the reinforcing portion 42 and the protector portion 43. Like this, the reinforcing portion 42 and the protector portion 43 are provided separately and integrated by the outer layer portion 44. Therefore, by cutting the boundary portion between the reinforcing portion 42 and the protector portion 43 in the outer layer portion 44, the cover portion 41 can be easily detached from the cylindrical portion 40.

Figure 4A:
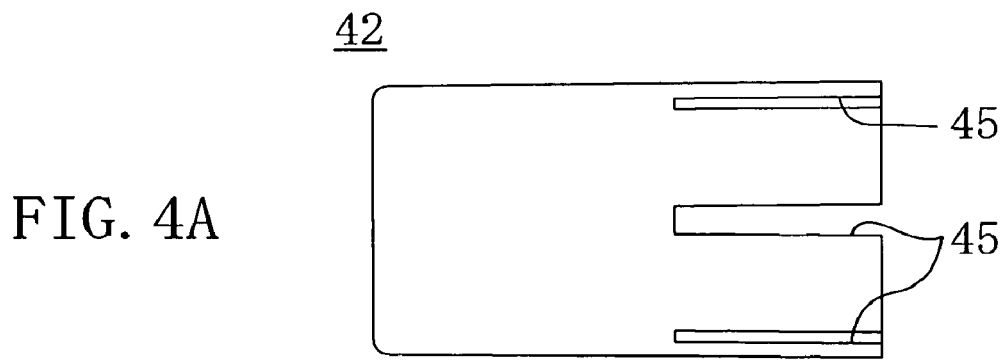
FIG. 4A is a side view.
Figure 4B:
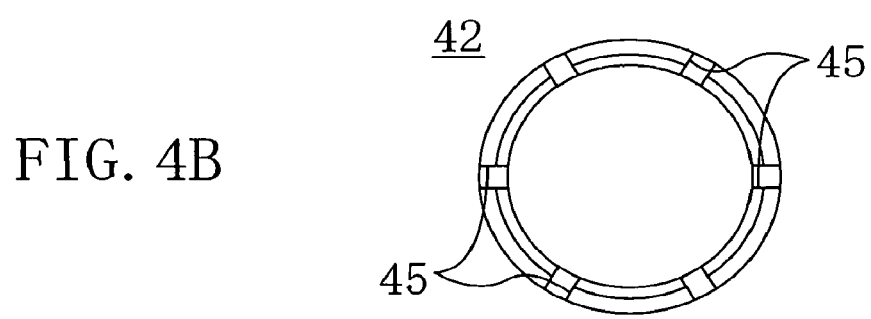
FIG. 4B is a back view when viewed from the proximal end side.
Figure 4C:
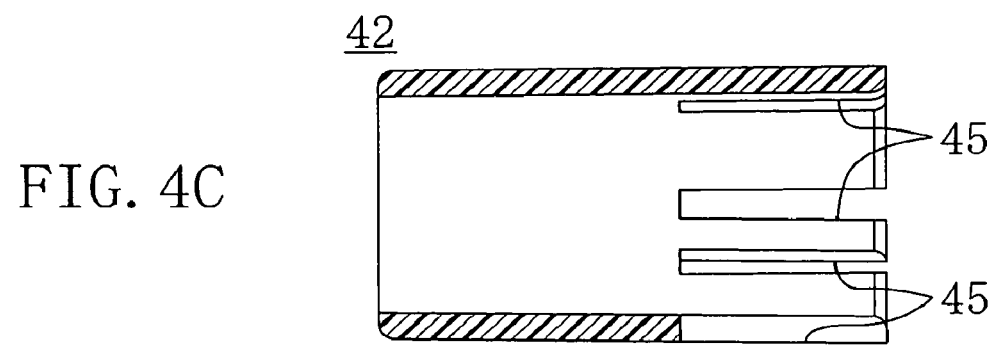
FIG. 4C is a sectional view.

The above-described reinforcing portion 42 is formed by injection-molding polypropylene, for example. As shown in FIG. 4, in about a half of the peripheral wall of the reinforcing portion 42 on the proximal end side, a large number, of notches 45 extending towards the center line direction, are formed with a distance provided therebetween in the circumferential direction. With this, the peripheral wall on the proximal end side is divided into a plurality of sections in the circumferential direction. By dividing the peripheral wall on the proximal end side, the proximal end of the peripheral wall becomes likely to bend and deform to be displaced towards the outer or inner side in the radial direction, when the reinforcing portion 42 is pressed towards the center line direction. As a result, the reinforcing portion 42 can be easily crushed and deformed towards the center line direction.

The above-described protector portion 43 is formed by injection-molding polypropylene, for example. As shown in FIG. 1 and FIG. 3, it is formed thicker than the above-described reinforcing portion 42. The distal end face of the protector 43 is constituted with a curving face that curves towards the outer side. The proximal end side of the protector portion 43 is formed in a tapered shape where the diameter expands towards the proximal end side. The outer face of this proximal end part continues to the outer face of the above-described reinforcing portion 42. Further, the proximal end face of the protector portion 43 is formed to be closely fitted with the distal end face of the above-described reinforcing portion 42.

The above-described outer layer portion 44 is formed with a resin material that is softer than that of the protector portion 43. For example, silicon, polyvinyl chloride, or the like may be used as the resin material. The distal end part of the outer layer portion 44 is formed to curve by corresponding to the shape of the distal end part of the above-described protector portion 43, and it is formed thicker than other parts of the outer layer portion 44. By forming the outer layer portion 44 with a soft material as mentioned above, it becomes easy to be deformed by the external force. The outer layer portion 44 and proximal end side of the above-described reinforcing portion 43 together constitute a fragile portion of the present invention.

Further, an engaging portion 48 is provided on the outer face of the cylindrical portion 40, with which the piece A of the intestine is engaged when the anus-side piece A of the intestine is tied with the suture C. The engaging portion 48 is constituted with a first projected line 49 that projects from the outer layer portion 44 towards the outer side of the radial direction and extends in the circumferential direction, and a second projected line 50 that extends in the same manner from the first projected line 49 towards the proximal end side at a distant position. The height of the projection of the first projected line 49 is formed higher than that of the second projected line 50.

Further, a proximal end side projected portion 51, which projects towards the outer side of the radial direction and extends in the circumferential direction, is provided in the proximal end part of the cylindrical portion 40. The distal end in the projecting direction of the proximal end side projected portion 51 abuts against the inner face of the recessed portion 26 to prevent the cylindrical portion 40 from coming off from the recessed portion 26, when the cylindrical portion 40 is inserted to the recessed portion 26 of the device main body 21.

Figure 5A:
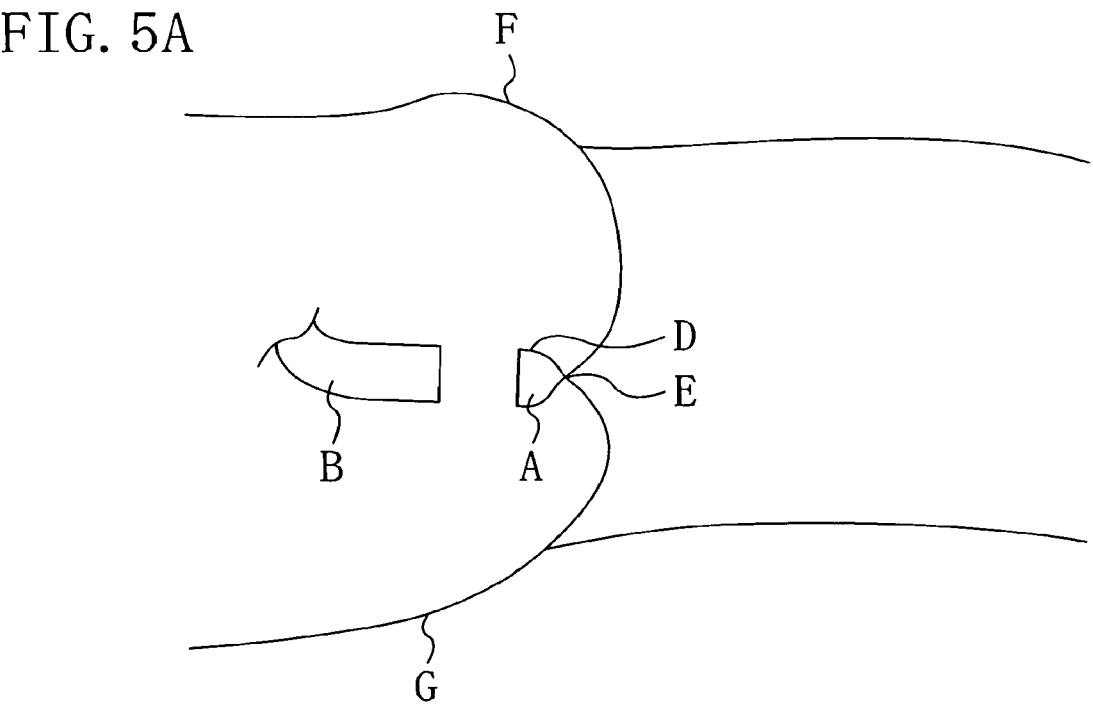
FIG. 5A is an illustration for describing the state where a diseased part is removed from the rectum.

Next, the point for using the above-described intestinal anastomotic surgery aid 1 will be described. This embodiment refers to the case of a surgical operation on a rectal cancer performed when there is a cancer contracted in the vicinity of the anus E of the rectum D, and explanations will be provided for the case where the anus-side piece A of the intestine and the piece B that is the sigmoid colon on the stomach side are anastomosed after removing the diseased part. FIG. 5A shows the state where the diseased part is removed, and each of the anus-side piece A of the intestine and the stomach-side piece B of the intestine is left open. Reference code F indicates the sacrum region and G indicates the abdominal region.

Figure 5B:
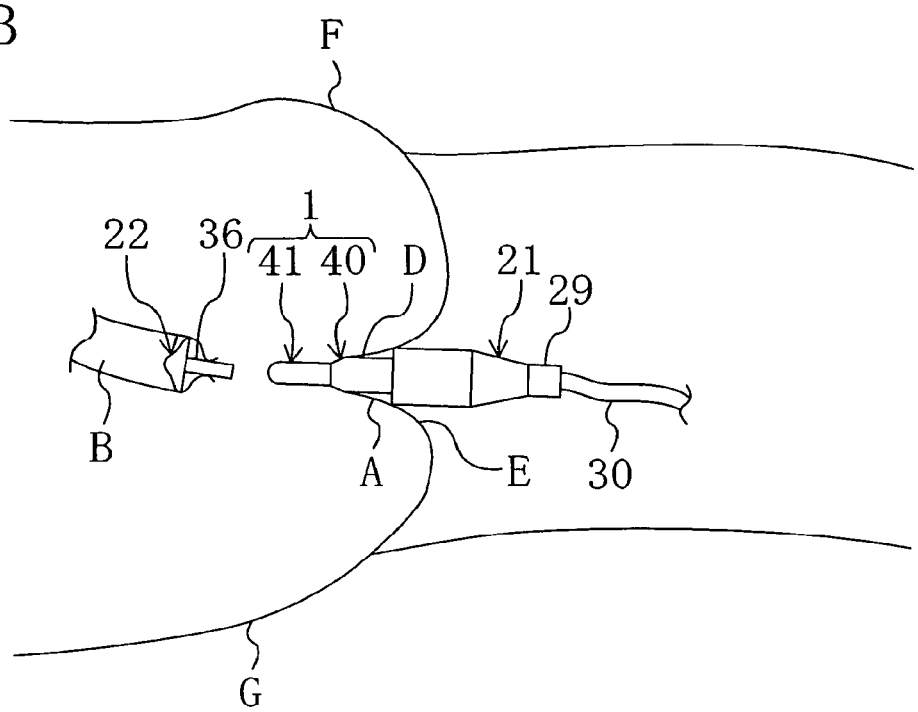
FIG. 5B is an illustration for describing the state where the main body of the anastomotic device is inserted to the anus-side piece of the intestine, and the head is inserted to the stomach-side piece of the intestine.

First, as shown in FIG. 1, the cylindrical portion 40 of the intestinal anastomotic surgery aid 1 is inserted to the recessed portion 26 of the device main body 21 to attach the aid 1 to the device main body 21. Then, the distal end side of the cover portion 41 of the intestinal anastomotic surgery aid 1 is inserted to the anus-side piece A of the intestine from the anus E until the device main body 21 reaches, a prescribed position, as shown in FIG. 5B. In this state, the engaging rod 28 of the device main body 21 is covered by the cover portion 41. Moreover, the distal end face of the cover portion 41 is curved, so that the engaging rod 28 does not abut against the side wall of the anus-side piece A of the intestine to stick therein. Further, the protector portion 43 is provided to the cover portion 41. Thus, the engaging rod 28 is prevented from piercing through the cover portion 41, so that the engaging rod 28 does not abut against the side wall A of the intestine. Furthermore, the protector portion 43 is covered by the soft outer layer portion 44. Moreover, the distal end part of the outer layer 44 is thicker than the other parts, so that the soft material is the one to come in contact with the side wall of the piece A of the intestine.

When the device main body 21 is inserted to the prescribed position, the device main body 21 and the cylindrical portion 40 are covered by the anus-side piece A of the intestine. Meanwhile, the cover portion 41 projects towards the outer side from the open end part of the anus-side piece A of the intestine. Then, the suture C that is tied in a loop in advance is moved from the distal end of the cover portion 41 towards the proximal end side to be hanged on the anus-side piece A of the intestine. Then, as shown in FIG. 6, the suture C is dropped between the first projected line 49 and the second projected line 50 to tie the anus-side piece A of the intestine to the cylindrical portion 40 tightly. At that time, the cylindrical portion 40 is reinforced by the reinforcing portion 42, so that the cylindrical portion 40 is not crushed towards the radial direction, and the anus-side piece A of the intestine is securely held to the cylindrical portion 40. Furthermore, even though the vicinity of the anus E of the rectum D is located in a deep area within the pelvis cavity, so that it cannot be visually checked and reached by hands, it is possible with the embodiment to hold it to the cylindrical portion 40 easily and securely by groping, since the suture C may simply be dropped between the two projected lines 49 and 50 for holding the anus-side piece A of the intestine to the cylindrical portion 40.

Further, since the cylindrical portion 40 has a shape to cover the engaging rod 28 and has a larger diameter than the engaging rod 28, it requires to pull only a shorter length of the anus-side piece A of the intestine compared to the conventional case where the anus side piece A of the intestine is held directly to the engaging rod 28. This makes it possible to have the piece A of the intestine held at the device main body 21 through the cylindrical portion 40, even if the length of the anus-side piece A of the intestine cannot be secured long enough because the diseased part in the vicinity of the anus E is cut out.

In the meantime, the head 22 is inserted from the swollen member 37 side of the head 22 to the stomach-side piece B of the intestine, and the projected portion 36 is extruded to the outer side from the open end part of the stomach-side piece B of the intestine. The open end part of the stomach-side piece B of the intestine is tied and held to the projected portion 36 with the suture C.

Figure 7:
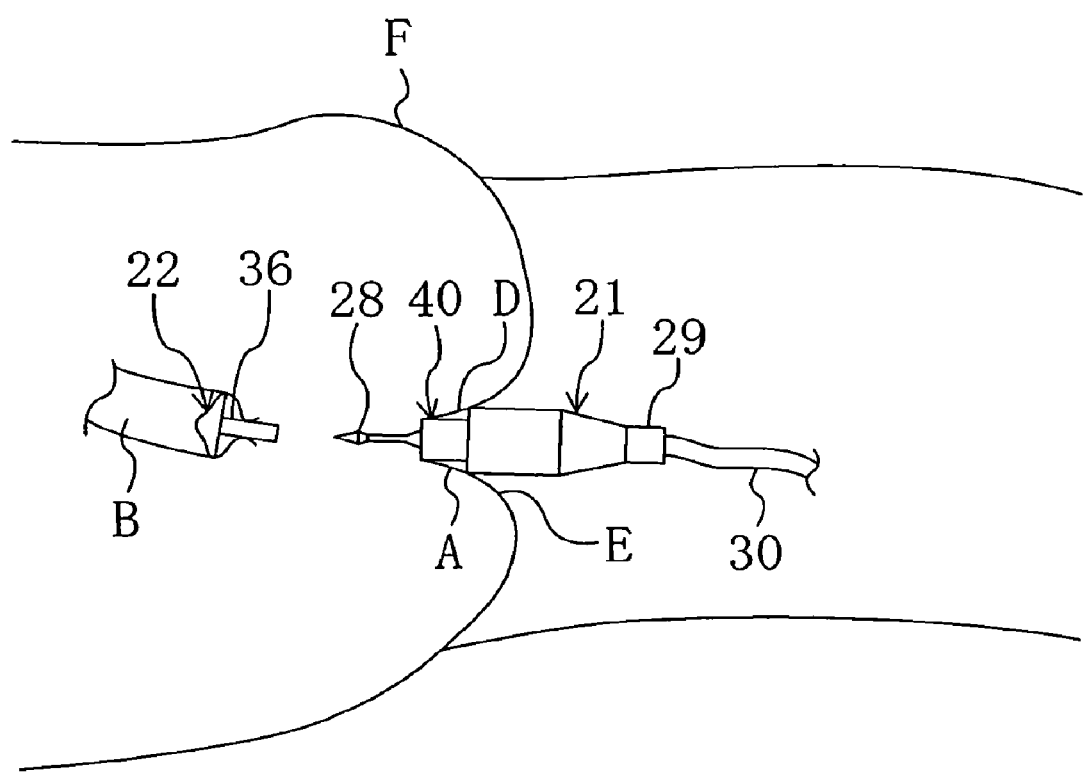
FIG. 7 is an illustration for describing the state where a cover portion is detached from the cylindrical portion.
Figure 8:
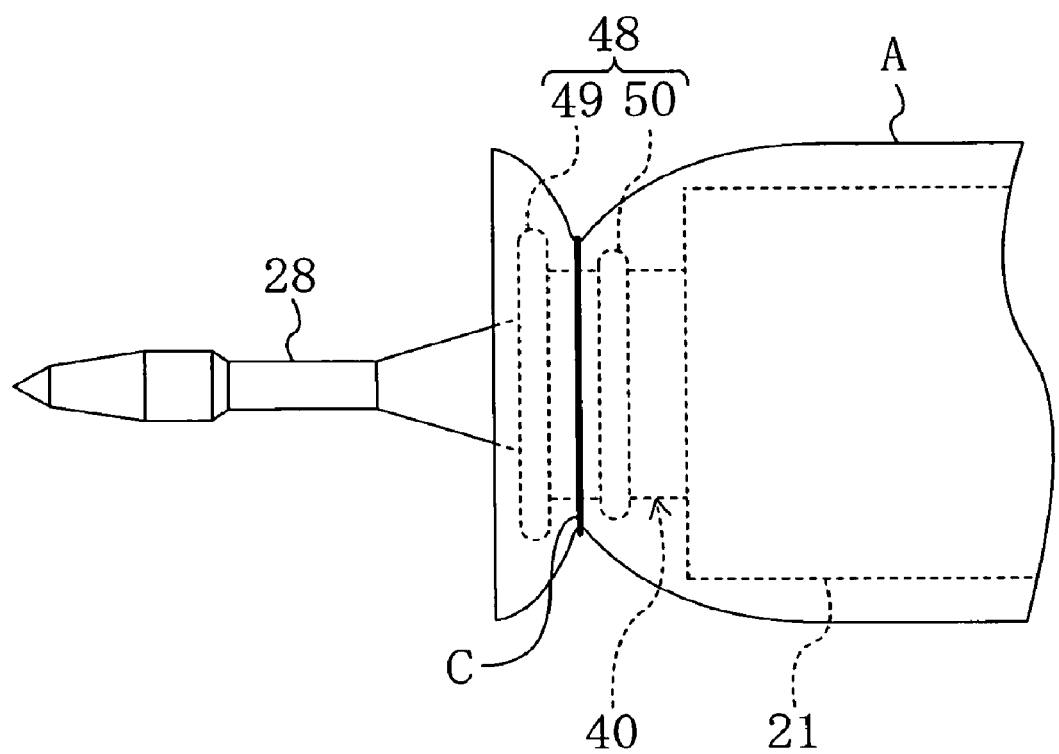
FIG. 8 is an enlarged view showing the vicinity of the anus-side piece of the intestine.
Figure 9A:
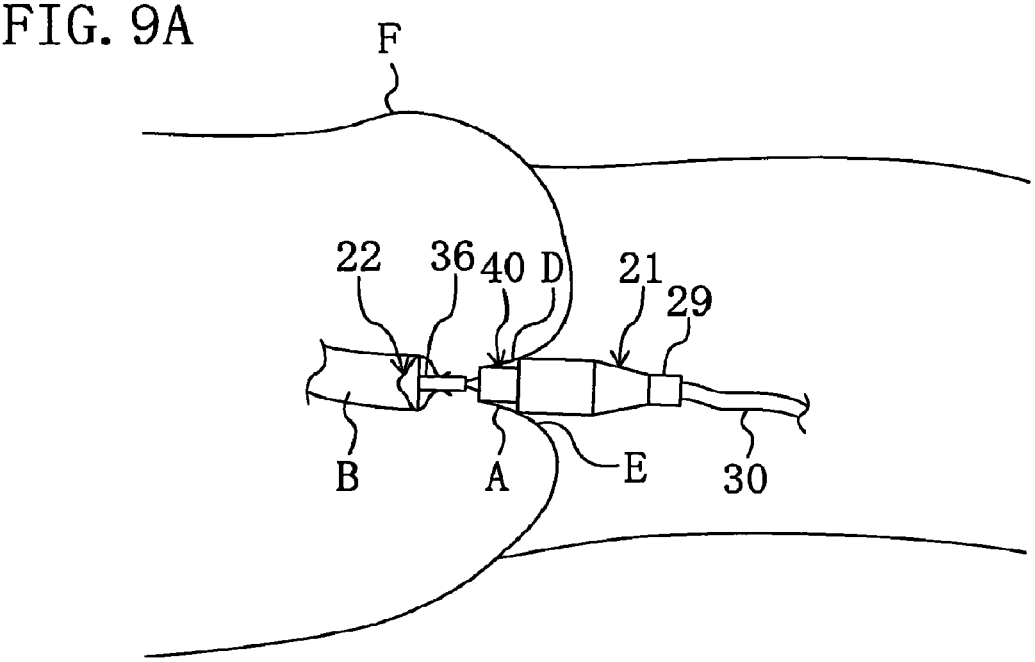
FIG. 9A is an illustration for describing the state where the head is engaged with the engaging rod.
Figure 9B:
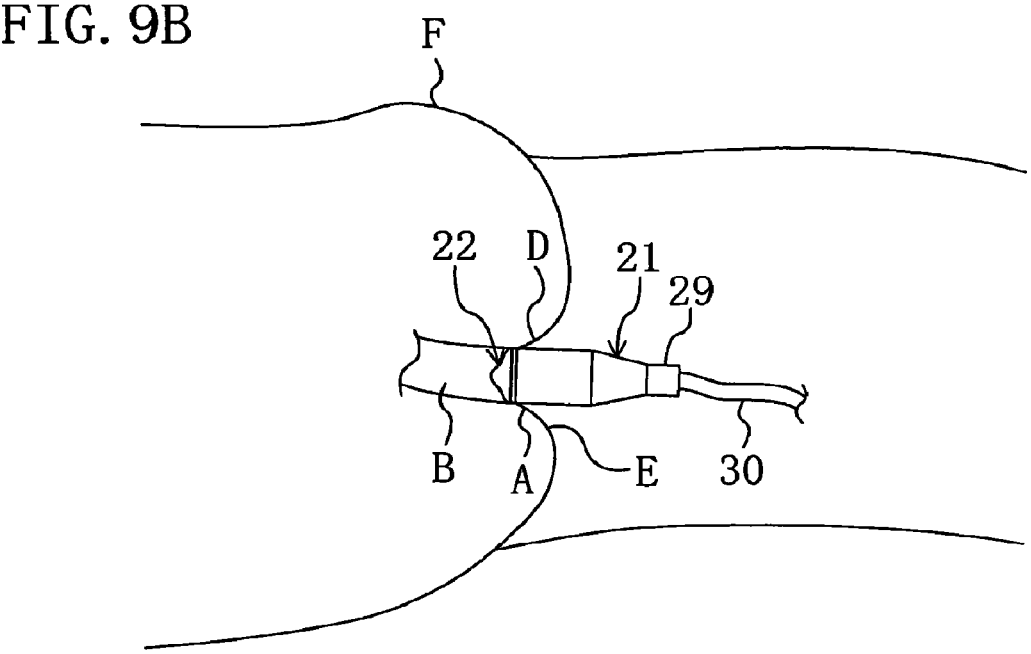
FIG. 9B is an illustration for describing the state where the anus-side piece and the stomach-side piece of the intestine are anastomosed.

Then, as shown in FIG. 7 and FIG. 8, the cover portion 41 is detached from the cylindrical portion 40 by cutting the boundary area between the reinforcing portion 42 and the protector portion 43 of the outer layer portion 44 by a scalpel, for example, in the circumferential direction. When the cover portion 41 is detached from the cylindrical portion 40, the distal end side of the engaging rod 28 is exposed. Then, as shown in FIG. 9A, the head 22 is brought closer to the device main body 21 to insert the engaging rod 28 to the inside the projected portion 36 of the head 22, so that it is engaged with the engaging rod 28.

By supplying the electricity to the device main body 21 by the controller thereafter, the engaging rod 28 is retracted to the inside the device main body 21. With this, the head 22 comes close to the device main body 21, and the open end part of the anus-side piece A of the intestine and the open end part, of the stomach-side piece B of the intestine come in contact with each other.

When retracting the engaging rod 28, the anus-side piece A of the intestine does not slide on the outer face of the engaging rod 28 by the retracting, action of the engaging rod 28, since the anus-side piece A of the intestine is held on the outer face of the cylindrical portion 40. Therefore, the anastomosed part of the anus-side piece A, of the intestine is not to be deformed, and it becomes possible to locate the anastomosed part at a prescribed position of the device main body 21. As a result, the anastomosed part of the anus-side piece A of the intestine and that of the stomach-side piece B of the intestine can securely be fitted closely with each other.

Figure 10:
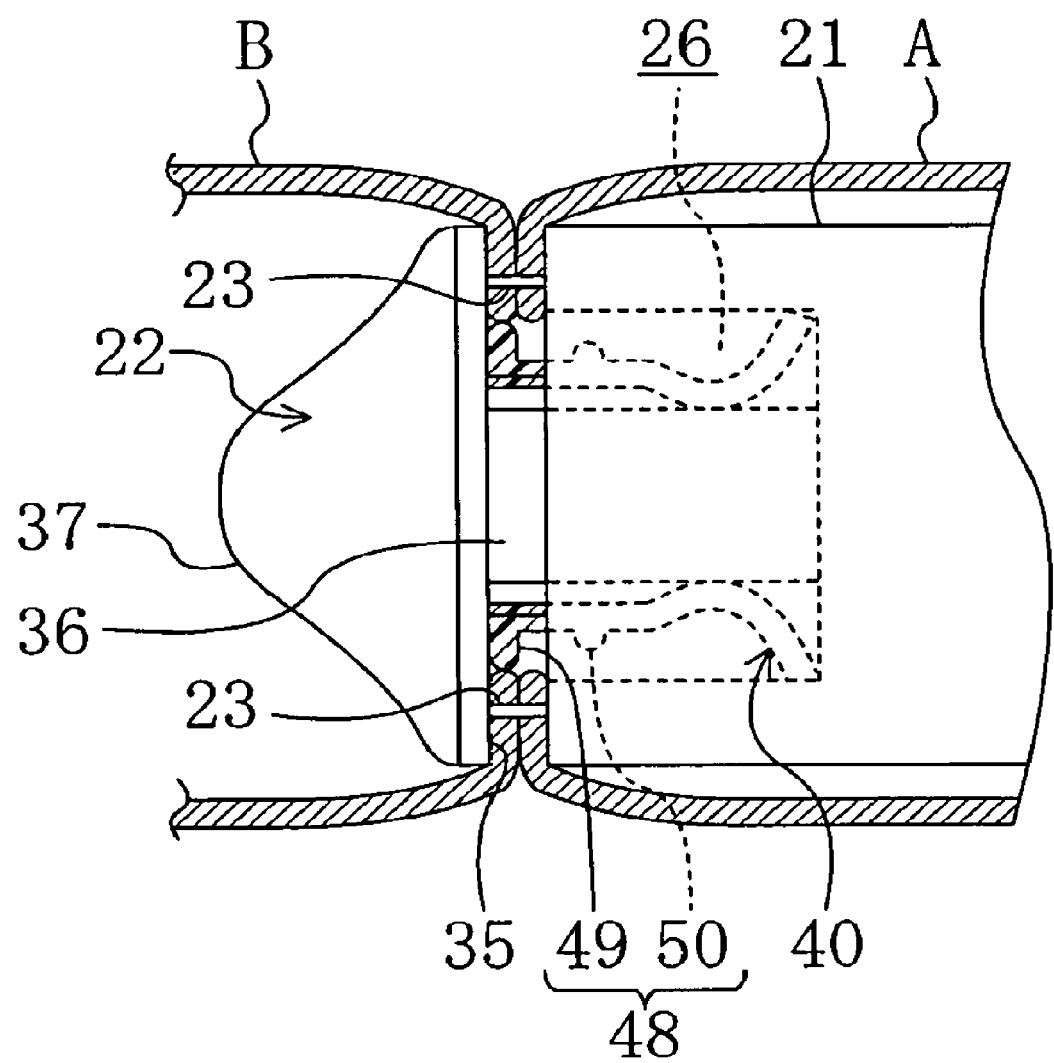
FIG. 10 is a fragmentary sectional view showing an enlarged view of the vicinity of the anastomosed part of FIG. 9B.

Further, when the head 22 is close to the device main body 21, as shown in FIG. 10, the cylindrical portion 40 is pressed towards the center line direction by the head 22 and the bottom face of the recessed portion 26 of the device main body 21. Because of the load imposed at this time, the peripheral wall of the reinforcing portion 42 is bent to be deformed, while the soft outer layer 44 is crushed to be deformed. With this, the cylindrical portion 40 is housed in the recessed portion 26 of the device main body 21 without hindering the head 22 from coming closer to the device main body 21.

Then, the staplers 23 struck out from the slits 24 of the device main body 21 pierce through the open end part of the anus-side piece A of the intestine and that of the stomach-side piece B of the intestine, and are bent by reaching at the pits 38 of the head 22, thereby anastomosing the anus-side piece A of the intestine and the stomach-side piece B of the intestine. At this time, the cutter 25 of the device main body 21 abuts against the head 22, and the regions of the anus-side piece A of the intestine and the stomach-side piece B of the intestine located on the inner side than the anastomosed part thereof are cut out and housed inside the recessed portion 26 of the device main body 21, although not shown.

By removing the device main body 21 and the head 22 from the anus E thereafter, the anastomotic surgery is completed.

Therefore, with the intestinal anastomotic surgery aid 1 according to this embodiment, it is possible to perform the anastomotic surgery by using the anastomotic device 20 even when the length of the anus-side piece A of the intestine is short because the diseased part in the vicinity of the anus E of the rectum D is cut out, since the anus-side piece A of the intestine is tied with the suture C to be held to the outer face of the cylindrical portion 40 that is formed to cover the engaging rod 28. Furthermore, the anus-side piece A of the intestine is held to the cylindrical portion 40 that is held to the device main body 21, so that the position of the anus-side piece A of the intestine is not shifted when the engaging rod 28 is retracted to the inside the device main body 21. Thus, the anus-side piece A of the intestine can be fitted closely to the stomach-side piece B of the intestine, and the both can be anastomosed in the desired manner.

Further, since the distal end side of the engaging rod 28 is covered by the cover portion 41, the device main body 21 can be, smoothly inserted to the anus-side piece A of the intestine.

Further, the protector portion 43 securely prevents the engaging rod 28 from piercing through the cover portion 41, so that the anastomotic surgery can be performed safely. Furthermore, the soft outer layer portion 44 is the one that is abutted against the side wall of the piece A of the intestine when inserting the device main body 21 to the anus-side piece A of the intestine, so that the anastomotic surgery can be performed low-invasively.

Furthermore, since the cylindrical portion 40 is reinforced by the reinforcing portion 42, the anus-side piece A of the intestine can be tied tightly to the cylindrical portion 40 with the suture C. With this, the anus-side piece A of the intestine is not to come off from the cylindrical portion 40, so that the anus-side piece A of the intestine and the stomach-side piece B of the intestine can be anastomosed securely.

Further, the cylindrical portion 40 is crushed to be deformed towards the center line direction and is housed in the recessed portion 26, when the head 22 is drawn towards the device main body 21. Therefore, the cylindrical portion 40 does not intervene in anastomosing the anus-side piece A of the intestine and the stomach-side piece B of the intestine, and the both can be anastomosed smoothly.

Moreover, since the anus-side piece A of the intestine tied to the cylindrical portion 40 is engaged with the engaging portion 48, it is possible to securely prevent the anus-side piece A of the intestine from being shifted from the prescribed position. Further, the anus-side piece A of the intestine can be securely held at the prescribed position in the pelvis cavity where it is difficult to perform a hand work.

Figure 11:
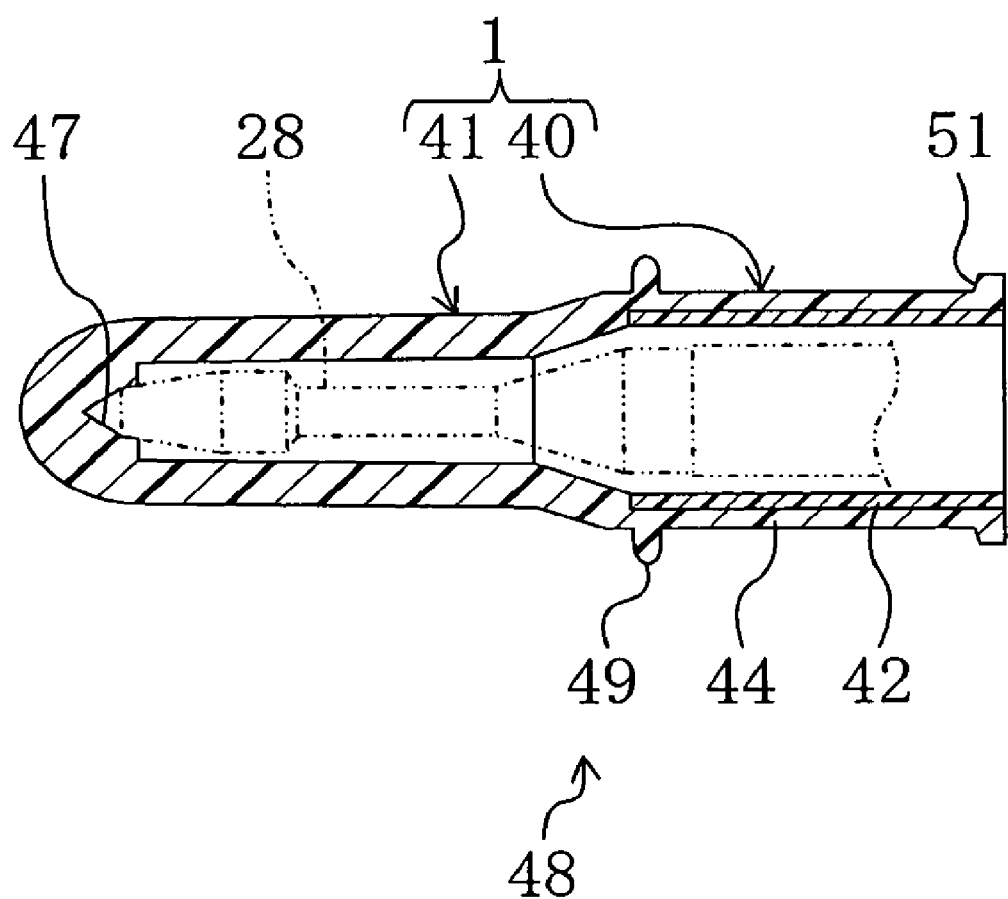
FIG. 11 is an illustration of a modification example of the first embodiment, which corresponds to FIG. 3.
Figure 12:
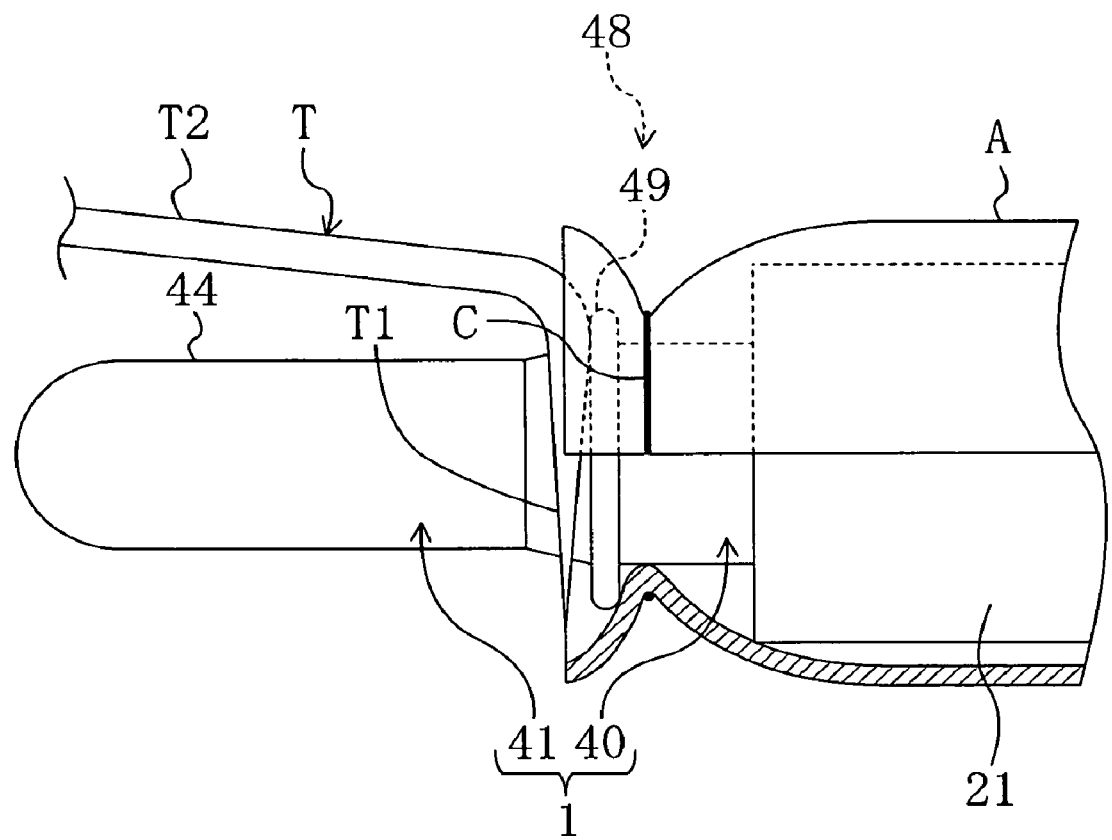
FIG. 12 is a fragmentary sectional view of the modification example of the first embodiment, which shows an enlarged view of the state right before the anus-side piece of the intestine is tied to the cylindrical portion and the cover portion is cut out.

As in a modification example shown in FIG. 11 and FIG. 12, it is also possible to constitute the engaging portion 48 only with a single projected line 49, and to constitute the cover portion by a single-layered structure that is formed by molding silicon, polyvinyl chloride, or the like, for example. This cover portion 41 is integrated with the outer layer portion 44 of the cylindrical portion 40. Further, the distal end part of the cover portion 41 is formed thick, and a distal end side recessed portion 47 to which the distal end part of the above-described engaging rod 28 is fitted is formed on the inner face thereof. Therefore, when the intestinal anastomotic surgery aid 1 is held to the device main body 21, the distal end part of the engaging rod 28 is fitted in the distal end side recessed portion 47 of the intestinal anastomotic surgery aid 1, and the distal end side of the intestinal anastomotic surgery aid 1 is supported by the engaging rod 28. With this, the distal end side of the intestinal anastomotic surgery aid 1 is stabilized when inserting the anus-side piece A of the intestine to the device main body 21. Furthermore, since the distal end side of the cover portion 41 is thick, the engaging rod 28 does not damage the inner wall of the piece A of the intestine, when inserting the intestinal anastomotic surgery aid 1 to the anus-side piece A of the intestine from the anus E.

Further, in this modification example, when the anus-side piece A of the intestine is tied to the cylindrical portion 40 with the suture C, the suture C is hanged to the side closer to the based end of the of the intestinal anastomotic surgery aid 1 than the projected line 49. With this, the anus-side piece A of the intestine can be easily and securely held to the cylindrical portion 40 by groping.

Furthermore, in this modification example, a pair of scissors T is used when detaching the cover portion 41 from the cylindrical portion 40, as shown in FIG. 12. The scissors T are so-called right-angle scissors that are formed in such a manner that a blade T1 comes substantially at right angle with respect to an operation portion T2, which are used in general in medical scenes. The blade T1 is inserted from the stomach side to the anus-side piece A of the intestine to be pressed against the projected line 49, while keeping the blade T1 of the scissors T in an open state. With this, the position of the blade T1 of the scissors T comes at the end part of the cylindrical portion 40 of the cover portion 41. Thereafter, the cover portion 41 can be cut by operating the scissors T after housing the engaging rod 28 to the device main body 21 once. After cutting the cover portion 41, the engaging rod 28 is driven out. By cutting the cover portion 41 by using the scissors T in this manner, the cutting process of the cover portion 41 can be performed more safely and quickly compared to the case of using the above-described scalpel.

Second Embodiment

Figure 13A:
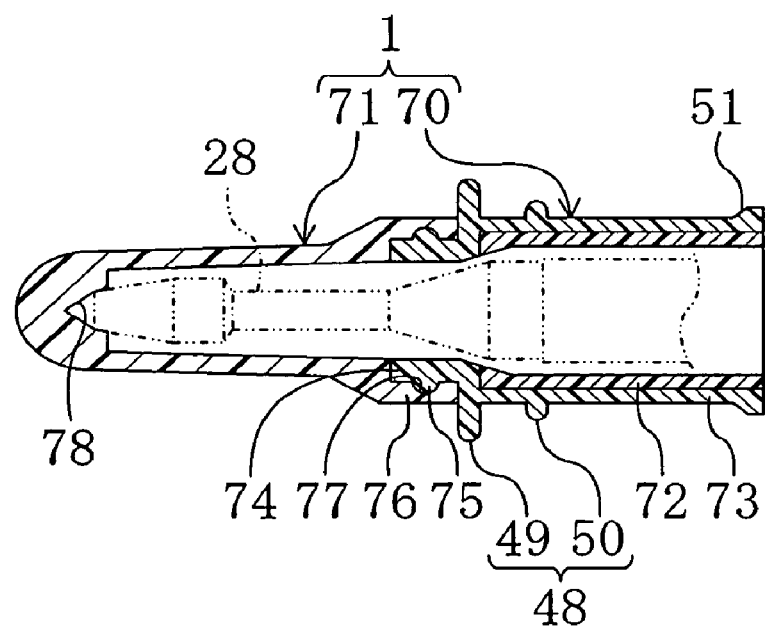
FIG. 13A is an illustration corresponding to FIG. 3.
Figure 13B:
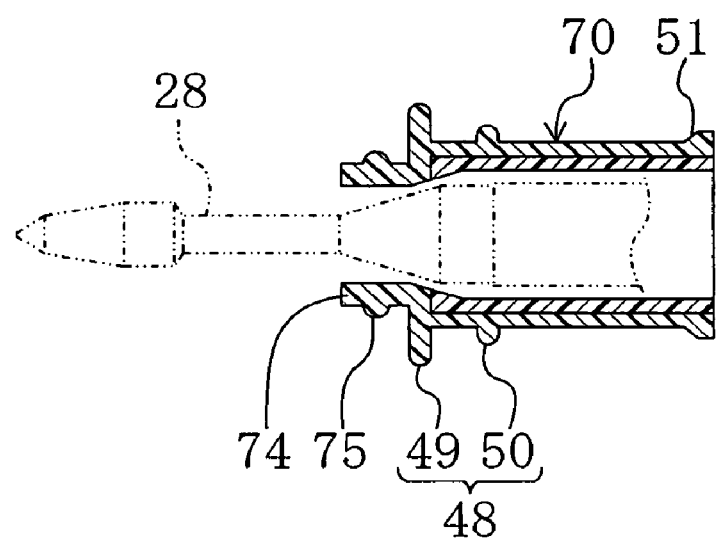
FIG. 13B is an illustration that corresponds to FIG. 3, which shows the state where the cover portion is detached.

FIG. 13 illustrates the intestinal anastomotic surgery aid 1 according to a second embodiment of the present invention. This intestinal anastomotic surgery aid 1 is different from that of the first embodiment only in respect that a cylindrical member 70 for covering the proximal end side of the engaging rod 28 and a cover member 71 for covering the distal end side of the engaging rod 28 are detachably united, and other parts are the same. Thus, the same reference numerals are applied to the components that are the same as those of the first embodiment, and descriptions thereof are omitted.

The cylindrical member 70 is formed in a double-layered structure of a reinforcing portion 72 and an outer layer portion 73 like the cylindrical portion of the first embodiment, while the cover member 71 is formed in a single-layered structure. Further, although not shown in the drawing, a large number of notches extending towards the center line direction are formed in about a half the peripheral wall of the above-described reinforcing portion 72 on the proximal end side, and the area of about a half the cylindrical member 70 on the proximal end side constitutes a fragile portion of the present invention. The outer face of the cylindrical member 70 may be covered by a material that is softer than the material used for forming the cylindrical member 70.

A ring-shaped extension portion 74 that extends towards the cover member 71 than towards the distal end part of the reinforcing portion 72 is provided on the outer layer portion 73 of the above-described cylindrical member 70. A protrusion 75 that projects towards, the outer side of the radial direction is formed on the outer face of the extension portion 74.

In the meantime, the cover member 71 is, formed by injection-molding polypropylene, for example, into a cylindrical shape with a bottom. The cover member 71 is provided with a ring-shaped fitting portion 76 that is fitted on the outer side of the above-described extension portion 74. The inside diameter of the fitting portion 76 is set to be slightly smaller than the outer diameter of the above-described extension portion 74. A base-side recessed portion 77 with which the protrusion 75 of the above-described extension portion 74 is engaged is formed on the inner face of the fitting portion 76.

When attaching the above-described cover member 71 to the cylindrical member 70, the extension portion 74 of the cylindrical member 70 is inserted into the fitting portion 76 of the cover member 71 to engage the protrusion 75 with the proximal end side recessed portion 77. In the meantime, when detaching the cover member 71 from the cylindrical member 70, the cover member 71 is pulled out in such a manner that the extension portion 74 comes off from the fitting portion 76. Thus, the protrusion 75 is released from the proximal end side recessed portion 77 for allowing the cover member 71 to be detached from the cylindrical member 70. Since the protrusion 75 is formed in the extension portion 74 of the soft outer layer portion 73, the extension portion 74 elastically changes its shape for enabling the cover member 71 to be attached and detached with respect to the cylindrical member 71 smoothly.

Further, the distal end part of the cover member 71 is formed thick, and a distal end side recessed portion 78 to which the distal end part of the above-described engaging rod 28 is fitted is formed on the inner face thereof. Therefore, when the intestinal anastomotic surgery aid 1 is held to the device main body 21, the distal end part of the engaging rod 28 is fitted in the distal end side recessed portion 78 of the intestinal anastomotic surgery aid 1, and the distal end side of the intestinal anastomotic surgery aid 1 is supported by the engaging rod 28. With this, the distal end side of the intestinal anastomotic surgery aid 1 is stabilized when inserting the anus-side piece A of the intestine to the device main body 21. Furthermore, since the distal end side of the cover member 71 is thick, the above-described engaging rod 28 does not damage the inner wall of the piece A of the intestine.

The point for using the above-described intestinal anastomotic surgery aid 1 is as follows. First, the cover member 71 is attached to the cylindrical member 70, and the cylindrical member 70 is held to the device main body 21. Then, after inserting the device main body 21 to a prescribed position of the anus-side piece A of the intestine, the open end part of the anus-side piece A of the intestine is held to the cylindrical member 70. At the same time, the cover member 71 is detached from the cylindrical member 70 and the projected portion 36 of the head 22 is engaged with the engaging rod 28 of the device main body 21, thereby anastomosing the anus-side piece A of the intestine and the stomach-side piece B of the intestine.

Therefore, as in the case of the first embodiment, it is possible with the intestinal anastomotic surgery aid 1 according to this embodiment to perform the anastomotic surgery by using the anastomotic device 20, even when the length of the anus-side piece A of the intestine is short because the diseased part in the vicinity of the anus E of the rectum D is cut out. At the same time, the position of the anus-side piece A of the intestine is not shifted when the engaging rod 28 of the device main body 21 is retracted to the inside the device main body 21, so that the anus-side piece A of the intestine and the stomach-side piece B of the intestine can be anastomosed in the desired manner.

The aforementioned second embodiment has been described by referring to the case where the intestinal anastomotic surgery aid 1 is attached to the anastomotic device 20 in which the engaging rod 28 is provided to the device main body 21. However, the intestinal anastomotic surgery aid 1 of the present invention can also be used for an anastomotic device in which the engaging rod is provided to the head. Although not shown in the drawing, this anastomotic device is so formed that the engaging rod of the head is inserted into the device main body to be engaged therein. In this case, an intestinal anastomotic surgery aid having no cover member may be used.

Further, the intestinal anastomotic surgery aid 1 of the present invention can be used not only for an intestinal anastomotic surgery operated for a rectal cancer but also for the case where the cutout intestines are anastomosed by using the anastomotic device 20.

Furthermore, the intestinal anastomotic surgery aid 1 of the present invention can also be used for the case where the side-to-end anastomosis is performed as in the conventional case, in addition to the case of the above-described embodiments where the end-to-end anastomosis is performed. That is, after inserting the head 22 to the stomach-side piece B of the intestine, the open end part of the piece B of the intestine is closed by suturing. At the same time, the projected portion 36 of the head 22 is projected out to the outer side by having it pierced through the side wall of the stomach-side piece B of the intestine, and the projected portion 36 is engaged, with the engaging rod 28 of the device main body 21 to anastomose the anus-side piece A of the intestine and the stomach-side piece B of the intestine.

Further, the engaging rod 28 is moved by the actuator of the device Main body 21 in each of the above-described embodiments. However, the engaging rod 28 may be moved manually, for example.

Furthermore, in each of the above-described embodiments, the engaging portion 48 is constituted with the first projected line 49 and the second projected line 50 continuing in the circumferential direction of the cylindrical portion 40 and the cylindrical member 70. However, the engaging portion 48 may not have to be formed continuously in the circumferential direction.

INDUSTRIAL APPLICABILITY

As described above, the intestinal anastomotic surgery aid of the present invention can be used for the case where an anastomotic surgery is performed by using an anastomotic device in a surgical operation of a rectal cancer, for example.

What is claimed is:

1. A method for performing anastomotic surgery to anastomose two cutout pieces of an intestine including an anus-side piece and a stomach-side piece using an anastomotic device including a device main body to be inserted from an anus to the anus-side piece of the cutout intestine and a head to be inserted to the stomach-side piece of the cutout intestine, the device main body and the head having an engaging rod projecting therefrom, the projecting engaging rod to engage with the other one of the device main body and the head and to be retracted into the device main body thereby anastomosing the anus-side piece and the stomach-side piece of the intestine, the method comprising:

providing an intestinal anastomotic surgery aid to be attached to the device main body of the anastomotic device, the intestinal anastomotic surgery aid including a cylindrical portion covering the device main body side of the engaging rod while maintaining a distance from an outer face of the engaging rod, and while the device main body and the engaging rod of the device main body are attached to each other, wherein the cylindrical portion is held to the device main body, and the anus-side piece of the intestine is held to an outer face of the cylindrical portion; and wherein the engaging rod is provided to project from the device main body towards an inserting direction of the device main body;

providing the intestinal anastomotic surgery aid with a detachable cover member to cover a distal end part of the engaging rod of the cylindrical portion;

wherein the cylindrical portion covers the engaging rod that projects from the device main body of the anastomotic device, and the cylindrical portion has a diameter larger than a diameter of the engaging rod projected from the device main body;

tying the anus-side piece of the intestine to the cylindrical portion using a suture; and sandwiching the cylindrical portion between the head and the device main body in an axial direction and crushing and deforming the cylindrical portion when the head of the anastomotic device is moved closer to the device main body to strike staplers;

wherein the cylindrical portion of intestinal anastomotic surgery aid has an outer circumference provided with projected lines with which the intestine tied by the suture is engaged.

2. A method for performing anastomotic surgery to anastomose two cutout pieces of an intestine including an anus-side piece and a stomach-side piece using an anastomotic device including a device main body inserted from an anus to the anus-side piece of the cutout intestine and a head inserted to the stomach-side piece of the cutout intestine, the device main body having an engaging rod projecting therefrom, the projecting engaging rod then being engaged with the head and retracted into the device main body thereby anastomosing the anus-side piece and the stomach-side piece of the intestine, the method comprising:

providing intestinal anastomotic surgery aid;

attaching the intestinal anastomotic surgery aid to the device main body of the anastomotic device, the intestinal anastomotic surgery aid including a cylindrical portion that covers the device main body side of the engaging rod while maintaining a distance from an outer face of the engaging rod, and while the device main body and the engaging rod are attached to each other; and providing the intestinal anastomotic surgery aid with a cover portion to cover a distal end part of the engaging rod by extending from the cylindrical portion towards the distal end side of the engaging rod;

wherein the cylindrical member is held to the device main body, and the anus-side piece of the intestine is held to an outer face of the cylindrical portion;

wherein the cover portion is detachably integrated with the cylindrical portion;

wherein the cylindrical portion covers the engaging rod that projects from the device main body of the anastomotic device, and the cylindrical portion has a diameter larger than a diameter of the engaging rod projected from the device main body;

tying the anus-side piece of the intestine to the cylindrical portion using a suture; and sandwiching the cylindrical portion between the head and the device main body in an axial direction and crushing and deforming the cylindrical portion when the head of the anastomotic device is moved closer to the device main body to strike staplers;

wherein the cylindrical portion of intestinal anastomotic surgery aid has an outer circumference provided with projected lines with which the intestine tied by the suture is engaged.

3. The method for performing an intestinal anastomotic surgery according to claim 2, further comprising providing the cover portion with a protector portion to prevent the distal end part of the engaging rod from piercing therethrough.

4. The method for performing an intestinal anastomotic surgery according to claim 3, further comprising covering an outer face of the protector portion by a material that is softer than a material used for forming the protector portion.

* * * * *